United States Patent [19]

Hukuhara et al.

[11] Patent Number: 5,073,343
[45] Date of Patent: Dec. 17, 1991

[54] APPARATUS FOR MEASURING A LIQUID SPECIMEN

[75] Inventors: Takahito Hukuhara; Teiichi Yabuta, both of Hyogoken, Japan

[73] Assignee: TOA Medical Electronics Co. Ltd., Hyogoku, Japan

[21] Appl. No.: 424,194

[22] Filed: Oct. 19, 1989

[30] Foreign Application Priority Data

Oct. 20, 1988 [JP] Japan ................... 63-264603

[51] Int. Cl.$^5$ .................. G01N 35/08; G01N 1/14
[52] U.S. Cl. ......................... 422/67; 422/63; 422/81; 73/864.17; 73/864.21
[58] Field of Search .................. 422/62, 67, 68, 73, 422/75, 81, 82, 100, 111, 115; 436/43, 50, 51, 66, 150; 73/864.13, 864.16–864.18, 864.21, 61.1; 141/130; 137/624.13

[56] References Cited

U.S. PATENT DOCUMENTS

| 3,726,144 | 4/1973 | Klein ......................... 422/100 |
| 3,799,844 | 3/1974 | Cambell et al. ............... 435/292 |
| 3,948,605 | 4/1976 | Atwood et al. ................ 422/63 |
| 3,948,607 | 4/1976 | Atwood et al. ................ 422/63 |
| 3,991,055 | 11/1976 | Godin et al. ................ 422/100 |
| 4,526,046 | 7/1985 | Oberli ....................... 73/864.16 |
| 4,710,355 | 12/1987 | Ushikubo ..................... 422/103 |
| 4,729,876 | 3/1988 | Hennessy et al. .............. 422/103 |

FOREIGN PATENT DOCUMENTS 8700280 1/1987 World Int. Prop. O. .......... 422/100

Primary Examiner—Robert J. Warden
Assistant Examiner—Howard Hampel
Attorney, Agent, or Firm—Morrison Law Firm

[57] ABSTRACT

A control system for a particle detector for detecting particles of blood components in an electrolyte employs sets of cams mounted on one-way clutches, which are positioned on a shaft of a motor. When the shaft is rotated by the motor in a clockwise direction, one set of cams moves together with the shaft, and when the shaft is rotated in the counterclockwise direction, another set of cams rotates in the counterclockwise direction. The rotation of cams controls movement of pistons which, together with cavities, form syringes and valves interconnected with passages. The valves and syringes are operated in sequence to prepare a specimen for measurement, to perform the measurement, and to clean up and purge the system between measurements.

11 Claims, 5 Drawing Sheets

APPARATUS FOR MEASURING A LIQUID SPECIMEN

BACKGROUND OF THE INVENTION

The present invention relates to measuring devices and, more particularly, to apparatus for measuring a number of particles and an amount of pigment in a test liquid.

To measure the number and the size of blood components (leukocytes, corpuscles, etc.) in a blood sample, the prior art mixes the blood sample with an electrically conducting liquid (an electrolyte), and passes a fixed volume of the mixture through a minute hole. Electrodes on opposed sides of the minute hole pass an electric current through the mixture, and particularly through the hole. The electrical resistance of blood components is different from that of the electrolyte. As a result, when a particle of blood component passes through the minute hole, it partly blocks the minute hole, thereby changing the electrical resistance therethrough. A resulting pulse change in resistance is detected. The pulses are counted while the fixed quantity of the mixture is drawn through the minute hole to indicate the amount of blood component particles in the mixture. The amount of hemoglobin (red pigment) in the mixture is measured with a colorimeter.

When the number of leukocytes and the amount of hemoglobin are measured by conventional apparatus using a test mixture containing hemolyzed red blood corpuscles, two separate liquid routes are required: one for measuring the number of leukocytes, the other for measuring the amount of hemoglobin.

Therefore, the liquid routes of conventional devices are complicated and expensive. Conventional devices also require large amounts of test mixture and a large amount of liquid for cleanup between tests.

In addition, conventional fluid control systems and devices controlling operation of fluid circuits, as well as devices for moving various parts of control systems, are bulky and inconvenient. Elements of such control systems frequently use tubes.

Furthermore, testing of blood components is frequently done in a series of tests of different blood samples. Purging of the equipment between tests is required in preparation for the next test. An automated technique for performing the tests and for performing the cleanup is desirable.

OBJECTS AND SUMMARY OF THE INVENTION

Accordingly, it is an object of the invention to provide an automatic apparatus for measuring a liquid specimen which detects changes in the electrical resistance as a mixture of an electrolyte and blood components is drawn through a minute aperture.

It is a further object of the invention to provide an automatic apparatus for testing a liquid specimen which utilizes a compact and convenient control system.

Briefly stated, the present invention provides a control system for a particle detector for detecting particles of blood components in an electrolyte. The apparatus employs sets of cams mounted on one-way clutches, positioned on a shaft of a motor. When the shaft is rotated by the motor in a clockwise direction, one set of cams moves together with the shaft, and when the shaft is rotated in the counterclockwise direction, another set of cams rotates in the counterclockwise direction. The rotation of cams controls movement of pistons which, together with cavities, form syringes and valves interconnected with passages. The valves and syringes are operated in sequence to prepare a specimen for measurement, to perform the measurement, and to clean up and purge the system between measurements.

According to an embodiment of the invention, there is provided a control system for controlling work of an analyzer of a liquid specimen comprising: a plurality of cams, means for rotating the plurality of cams, a plurality of pistons mounted for moving in plurality of cavities, means for resiliently urging the plurality of pistons into contact with respective ones of the plurality of cams, at least a first of the plurality of pistons including means for displacing a fixed quantity of the liquid specimen, and at least some of a remainder of the pistons including means for forming valves controlling a flow of the liquid displaced by the first of the plurality of pistons.

According to a feature of the invention, there is provided a control system for controlling an analyzer of a liquid specimen comprising: a shaft, a first plurality of cams, a second plurality of cams, a first one-way clutch on the shaft, the first one-way clutch being of a type capable of transmitting torque from the shaft only during rotation of the shaft in a first direction, means for connecting torque from the first one-way clutch to the first plurality of cams, a second one-way clutch on the shaft, the second one-way clutch being of a type capable of transmitting torque from the shaft only during rotation of the shaft in a second direction, opposite to the first direction, means for connecting torque from the second one-way clutch to the second plurality of cams, a first plurality of pistons mounted for moving in a first plurality of cavities, the first plurality of pistons contacting the first plurality of cams, a second plurality of pistons mounted for movement in a second plurality of cavities, the second plurality of pistons contacting the second plurality of cams, means cooperating with at least some of the pistons for forming syringes effective for displacing a quantity of the liquid, and means cooperating with at least some of a remainder of the pistons mounted for forming valves controlling a flow of the liquid displaced by the syringes.

According to a further feature of the invention, there is provided a control system for controlling liquid flow in a particle detector, comprising: a plurality of cams, means for selectively rotating the plurality of cams in a right-hand and a left-hand direction, a plurality of pistons mounted for movement in a plurality of cavities, the plurality of pistons contacting the plurality of cams; at least one of the plurality of pistons and one of the plurality of cavities forming a syringe effective for displacing a fixed quantity of the liquid, and at least some of a remainder of the plurality pistons and the plurality of cavities forming valves controlling a flow of the liquid displaced by the syringe.

According to a still further feature of the invention, there is provided a control system for handling a specimen comprising: a syringe, a tube, means for actuating the syringe to draw a predetermined quantity of the specimen into the tube, and means for enlarging a capacity of the tube to a value sufficient to contain at least the predetermined quantity, whereby none of the specimen is drawn into the syringe.

According to a still further feature of the invention, there is provided a control system for handling a specimen comprising: a first syringe, a detector immersed in the specimen, a first tube from the first syringe to an interior of the detector, a second syringe, a second tube immersed in the specimen, a colorimeter, means for connecting the second tube to the second syringe, the means for connecting including means for passing a fluid through the colorimeter, and common means for driving the first syringe, the second syringe and the means for connecting.

According to a still further feature of the invention, there is provided apparatus for preparing a diluted mixture of a specimen and a diluting liquid comprising: a first syringe, a capacity of the first syringe being a first predetermined quantity, a second syringe, a capacity of the second syringe being a second predetermined quantity, at least one valve, means for selectively closing and opening the at least one valve, first means for drawing the first predetermined quantity of the specimen into the first syringe, second means for drawing the second predetermined quantity of the diluting fluid into the second syringe, means for expelling the first and second predetermined quantities from the first and second syringes through a common exit, means for commonly driving the first and second means for drawing, the means for expelling and the means for selectively closing and opening the at least one valve, the means for commonly driving including a motor driving a plurality of cams, the means for commonly driving including a first piston forming part of the first syringe, a second piston forming part of the second syringe and a third piston forming part of the valve, and the first, second and third pistons being in actuation contact with the plurality of cams.

According to a still further feature of the invention, there is provided apparatus comprising: a specimen dilution device, the specimen dilution device including first and second syringes, and at least a first valve, first means for driving the specimen dilution apparatus, a specimen measurement apparatus, second means for driving the specimen measurement apparatus, the first and second means for driving including a reversible common motor, means for connecting the reversible common motor to drive the first means for driving during rotation of the motor in a first direction, and means for connecting the reversible common motor to drive the second means for driving during rotation of the motor in a second direction, opposite to the first direction.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
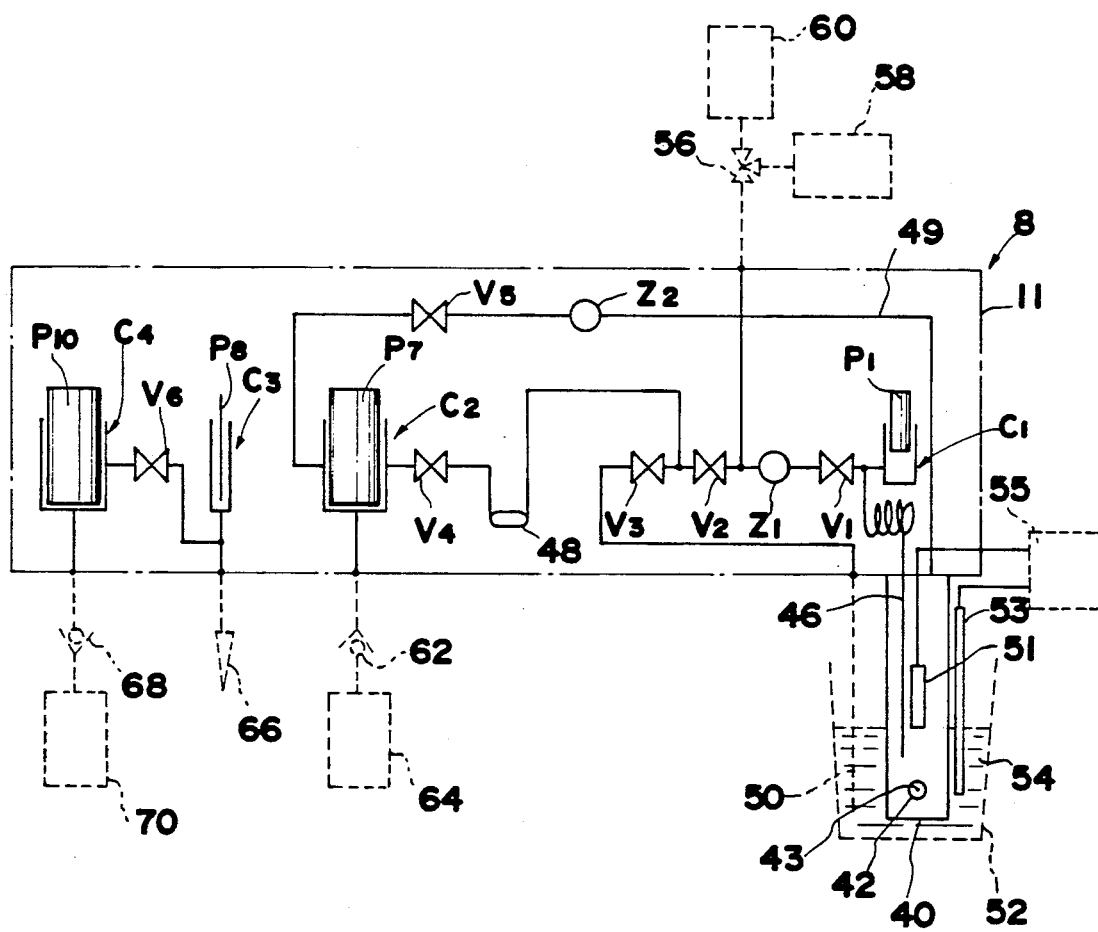
FIG. 1 is a schematic diagram of a fluid circuit of an apparatus for measuring a fluid according to an embodiment of the invention.

Referring to FIG. 1, there is shown, generally at 8, a liquid measurement system according to an embodiment of the invention. A detector 40, for measuring a number and size of particles in blood, is immersed in a diluted specimen 54 contained in a beaker 52. An electrolyte is used for the diluent in diluent specimen 54. The electrolyte and particles in the specimen to be measured have different electrical resistances. An aperture plate 42 has a minute hole 43 therein communicating between the outside and inside of cylindrical detector 40. A first electrode 51 is disposed inside detector 40, and a second electrode 53 is disposed in diluted specimen 54 outside detector 40. A detecting device 55 monitors the electrical resistance between electrode 51 and electrode 53.

A switchable valve 56 alternately connects fluid from a diluting liquid tub 60 and a syringe liquid tub 58 to the junction of an isolating chamber Z1 and a valve V2. A valve V1 leads from isolating chamber Z1 to a tube 46, whose end is located inside cylindrical detector 40, and to a syringe C1. A piston P1, in syringe C1, is driven to inspirate and aspirate fluid in sequence with other operations of liquid measurement system 8.

Valve V2 is connected through a valve V3 to a tube 50 whose end is immersed in diluted specimen 54 in beaker 52. A junction of valves V2 and V3 is connected through a colorimeter 48 and a valve V4 to a syringe C2. A piston P7 in syringe C2 is driven to inspirate and aspirate fluid in sequence with other operations of liquid measurement system 8. A line 49 is connected from cylindrical detector 40, through an isolating chamber Z2 and a valve V5 to syringe C2. A waste liquid tub 64 receives waste liquid from syringe C2. A check valve 62 prevents return flow of liquid from waste liquid tub 64 to syringe C2.

A separate portion of control system 11 prepares diluted specimens for use in the measurement operation. A syringe C4 receives diluting liquid (electrolyte) from a diluting liquid tub 70. A check valve 68 prevents return of the liquid to diluting liquid tub 70. A piston P10 is driven to inspirate and aspirate diluting liquid to and from syringe C4 in sequence with other operations. A specimen syringe C3 is connected to syringe C4 through a valve V6. Syringe C3 is also connected to a pipet 66. A piston P8 is driven to inspirate and aspirate the sample to be tested in sequence with other operations.

Isolating chambers Z1 and Z2 provide relatively large volumes in series with the flow of fluids, thereby isolating elements downstream thereof from upstream flow vibrations.

As will be further detailed hereinafter, three operations are performed during a cycle of control system 11. That is, 1) the number of particles in a fixed volume of diluted specimen 54 is counted, 2) the concentration of hemoglobin in diluted specimen 54 is measured, and 3) a new diluted specimen is prepared.

Figure 2:
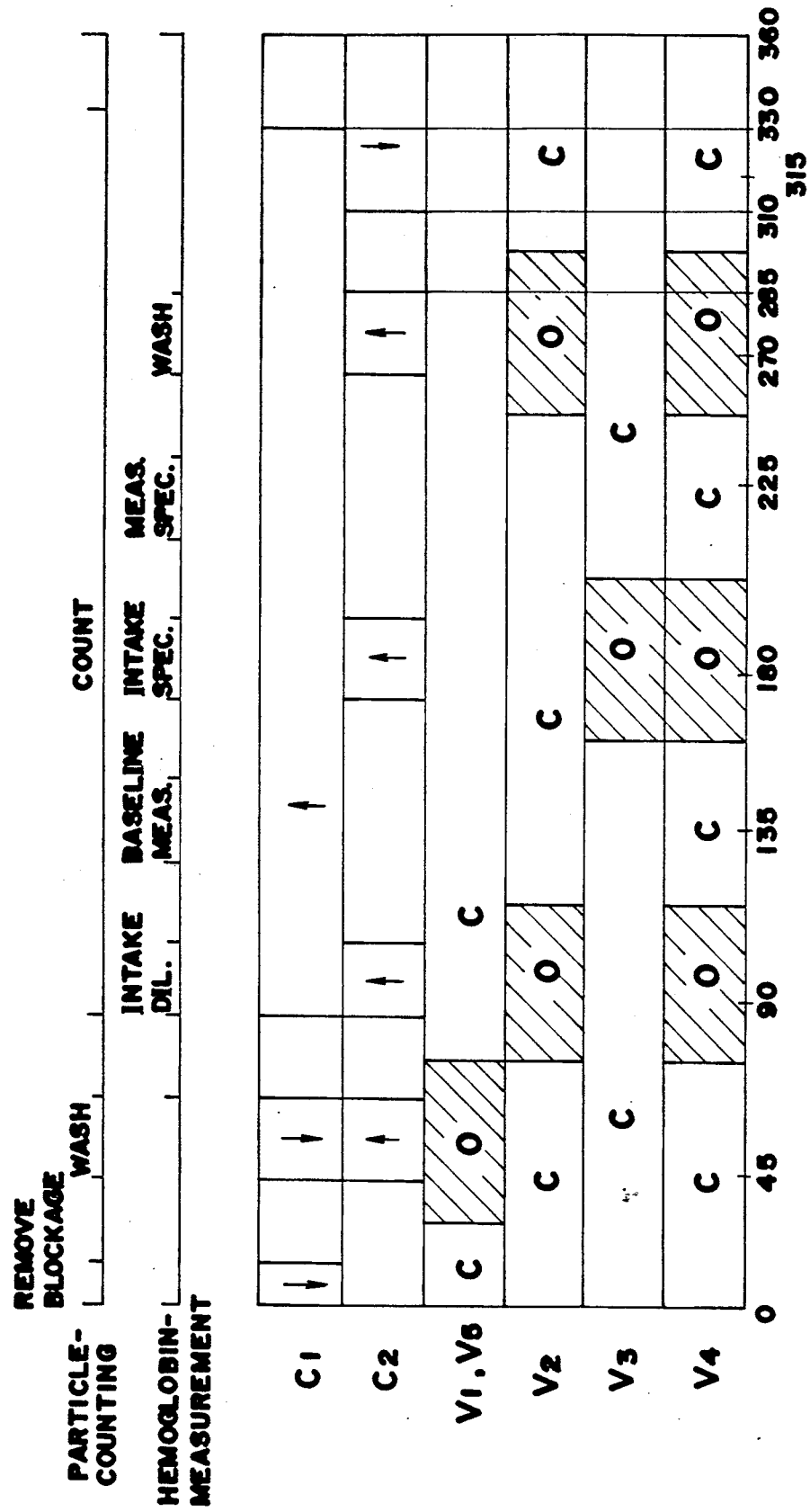
FIG. 2 is a sequence diagram for a portion of the control system of FIG. 2.

The timing diagram in FIG. 2 shows the sequence of valve and syringe actuations making up a cycle of the particle-counting and hemoglobin-measurement operations of liquid measurement system 8. The horizontal axis of the timing diagram is divided into 360 degrees, representing one cycle of the counting and measurement operations of control system 11. As will become apparent hereinafter, the sample-preparation operation takes place in a separate cycle.

Referring to FIGS. 1 and 2 together, from 0 to about 10 degrees, all valves remain closed and syringe C1 is moved in the aspirating direction. This forces some fluid from syringe C1 through tube 46 to clear any possible clogging particles therein. At about 20 degrees, valves V1 and V5 are opened. At about 40 degrees, syringe C2 is actuated in the aspirating direction. This causes a flow of syringe liquid to flow from syringe liquid tub 58, through isolating chamber Z1, valve V1, tube 46, cylindrical detector 40, line 49, isolating chamber Z2 and valve V5 to syringe C2. This flow purges these elements of materials remaining from a prior measurement. At the same time, syringe C1 is actuated in the aspirating direction to discharge any material remaining therein into the flow of material to syringe C2. This continues to about 60 degrees. At about 75 degrees, valves V1 and V5 are closed, and valves V2 and V4 are opened. At about 80 degrees, syringes C1 and C2 are actuated in the inspirating direction. Syringe C2 draws a clean supply of dilution liquid from diluting liquid tub 60 through valve V2, colorimeter 48 and valve V4. This purges any remaining material in colorimeter 48, and fills colorimeter 48 with a clean supply of dilution liquid which can then be used for a baseline measurement of light transmission. Syringe C1 begins to draw in a predetermined fixed quantity of diluted specimen 54 from which the number of particles are to be counted. Syringe C1 continues this inspiration from about 80 degrees to about 330 degrees. At about 100 degrees, syringe C2 stops inspiration.

At about 110 degrees, valves V2 and V4 are closed. At about 155 degrees, valves V3 and V4 are opened. At about 165 degrees, syringe C2 is actuated in the inspirating direction. This draws a sample of diluted specimen 54 through tube 50, valve V3, colorimeter 48 and valve V4 into syringe C2. As the sample of diluted specimen 54 is drawn through colorimeter 48, the amount of hemoglobin in diluted specimen 54 is determined by measuring the attenuation of light passing through the portion of diluted specimen 54 in colorimeter 48. At about 195 degrees, actuation of syringe C2 is halted. At about 200 degrees, valves V3 and V4 are closed.

At about 240 degrees, valves V2 and V4 are opened. At about 265 degrees, syringe C2 is actuated in the inspirating direction. This again draws syringe liquid from syringe liquid tub 58 through colorimeter 48 to purge colorimeter 48 in preparation for the next cycle. At about 285 degrees, actuation of syringe C2 is halted. At about 300 degrees, valves V2 and V4 are closed.

At about 310 degrees, syringe C2 is actuated in the ejecting direction. This expels all fluid accumulated in syringe C2 during prior phases through check valve 62 into waste liquid tub 64. This continues until 360 degrees.

At about 330 degrees, actuation of syringe C1 is halted. At this time, syringe C1 has completed inspiration of the predetermined fixed quantity of diluted specimen 54.

In addition to the above activities, the remaining part of control system 11 is engaged in preparing a diluted specimen for the next test. Initially, valve V6 is closed. Syringe C4 is actuated to draw in a predetermined fixed quantity of dilution fluid from diluting liquid tub 70. At the same time, syringe C3 is actuated to draw a predetermined fixed quantity of a specimen through pipet 66 from a container (not shown) containing the specimen.

The ratio of the quantities of liquid drawn into syringes C3 and C4 are such that, when the quantities are mixed, the desired dilution of the specimen is attained.

On completion of the inspiration of specimen and dilution fluid, valve V6 is opened and syringes C3 and C4 are actuated in the aspirating direction. The liquids therein are expelled through pipet 66 into a suitable container such as a beaker 52, in preparation for the next test.

Figure 3:
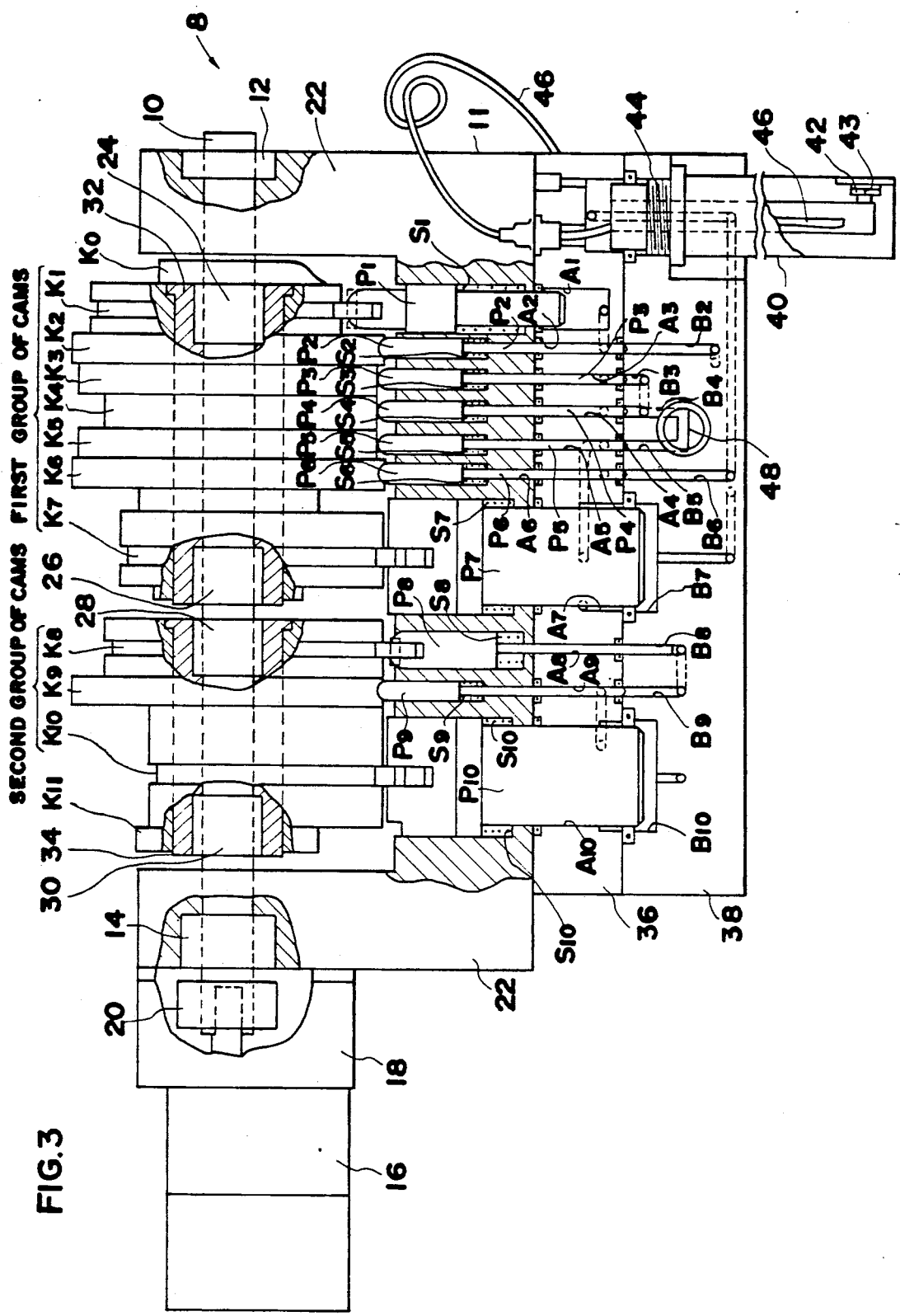
FIG. 3 is a side view, partly in cross-section, of a control system and detector according to an embodiment of the invention.

Referring now also to FIG. 3, control system 11 is implemented as a unitary assembly which includes all of valves V1-V6, syringes C1-C4, as well as the remainder of the elements shown schematically in FIG. 1. A supporter 22 contains first and second aligned bearings 12 and 14. A shaft 10 is rotatably supported in bearings 12 and 14. A reversible motor 16 is mounted on supporter 22 through a fixture 18. Motor 16 drives shaft 10 through a connecting member 20.

One-directional clutches 24 and 26 are disposed on shaft 10 within a cylindrical member 32. One-directional clutches 24 and 26 transmit torque to cylindrical member 32 only in response to rotation of shaft 10 in a single direction. A second pair of one-directional clutches 28 and 30 are disposed on shaft 10 within a second cylindrical member 34. When looking from the side of motor 16, one-directional clutches 24 and 26 transmit torque to cylindrical member 32 when shaft 10 spins in the right-hand direction (the direction of advance of a right-hand screw), and is incapable of transmitting torque when shaft 10 spins in the opposite direction. From the same perspective, one-directional clutches 28 and 30 and are capable of transmitting torque to cylindrical member 34 only when shaft 10 spins in the left-hand direction. One-directional clutches 24 and 26 are called a first group of one-direction clutches, and one-directional clutches 28 and 30 are called a second group of one-direction clutches.

Cams K1-K7 are fixed on cylindrical member 32, and are called a first group of cams. Cams K8-K10 are fixed on cylindrical member 34, and are called a second group of cams. The first group of cams perform the actuating functions for valves V1-V5 and syringes C1-C2. The second group of cams perform the actuating functions for valve V6 and syringes C3-C4.

When shaft 10 spins in the right-hand direction, one-directional clutches 24 and 26 drive cylindrical member 32, and cams K1-K7, affixed thereon, in the right-hand direction. During right-hand rotation of shaft 10, cylindrical member 34, and cams K8-K10 thereon, remain stationary.

When shaft 10 spins in the left-hand, cylindrical member 34, and cams K8-K10, affixed thereon, are also driven in the left-hand direction. During left-hand rotation of shaft 10, cylindrical member 32, and cams K1-K7, affixed thereon, remain stationary.

A plurality of holes in supporter 22 each contains one of pistons P1-P10. Each hole also includes one of springs S1-S10 to urge its respective piston upward into contact with its respective cam K1-K10.

Cam K0 and a sensor (not shown on the drawings) detect a rotation angle of cams in the first group, K1-K7. Cam K11 and a sensor (not shown on the drawings) detect a rotation angle of the second group of cams, K8-K10.

A cylinder block 36 is affixed below supporter 22. A cylinder block 38 is affixed below cylinder block 36. Cylinder block 36 includes cavities A1-A10, aligned with pistons P1-P10. Cylinder blocks 38 also includes cavities B2–B10 aligned with similarly subscripted cavities in cylinder block 36.

The pistons and cavities in FIG. 3 form all of the syringes and valves of FIG. 1.

Syringe C1 is formed by cavity A1 and piston P1. Syringe C2 is formed by cavities A7 and B7 and piston P7. Syringe C3 is formed by cavities A8 and B8 and piston P8. Syringe C4 is formed by cavities A10 and B10 and piston P10.

Valve V1 is formed by piston P2 and cavities A2 and B2. Valve V2 is formed by piston P3 and cavities A3 and B3. Valve V3 is formed by piston P4 and cavities A4 and B4. Valve V4 is formed by piston P5 and cavities A5 and B5. Valve V5 is formed by piston P6 and cavities A6 and B6. Valve V6 is formed by piston P9 and cavities A9 and B9.

The operation of the fluid circuit is explained below.

A liquid specimen is prepared during rotation of shaft 10 in the left-hand direction. Cams K1–K7 of the first group of cams remain stationary while cams K8–K10 of the second group of cams spin in the left-hand direction. Cam K9 initially holds piston P9 stationary in the closed position, thus maintaining valve V6 closed. Syringe C4 draws in a predetermined amount (e.g. 5 ml) of diluting liquid from diluting liquid tub 70. At the same time, syringe C3 draws in a predetermined amount (e.g. 20 microliters) of blood, which is the liquid specimen, from pipet 66. When shaft 10 reaches a predetermined angle in its left-hand rotation (e.g. 150 degrees), cam K9 moves piston P9 upward into the open position of valve V6. At about this time cams K8 and K10 begin urging pistons P8 and P10 in the downward direction to force the fluids from syringes C3 and C4 out of control system 11 through pipet 66 and into an external container (not shown). When shaft 10 reaches its original rotational position, cam K11, together with its sensor, senses this condition and halts left-hand rotation of motor 16, thereby ending the sample-preparation part of the operation.

Motor 16 is then driven through a cycle in the right-hand direction to produce the valve and syringe actions for counting and measuring described in the foregoing. Upon shaft 10 returning to its initial rotational position, cam K0, with its detector, terminate right-hand rotation of motor 16, thereby completing the counting and measuring operation.

In one method of using the apparatus, red blood corpuscles are hemolyzed, and hemoglobin is eluted by adding a small amount (e.g. 100 microliters) of a hemolyzing liquid drop by drop to the mixture in a beaker. Leukocytes are not hemolyzed. Diluted specimen 54 is diluted about 250 times.

The volume capacity of tube 46 can be increased to make it greater than the predetermined fixed quantity of fluid drawn in by syringe C1 to perform the measurement of particles in diluted specimen 54. The volume capacity of syringe C1 is increased by coiling tube 46 to increase its length. In this way, diluted specimen 54 is prevented from entering syringe C1, thus preventing contamination of syringe C1.

The cylinders used in the invention do not have to be separated, and may be constructed as desired. If it is desired to count the number of leukocytes and the amount of hemoglobin in a predetermined fixed quantity of the specimen, hemolysis is necessary. However, hemolysis is not required to count the number of red blood corpuscles. To count the number of red blood corpuscles, the prepared diluted specimen is further diluted about 62,500 times and placed in beaker 52. The difference in size between leukocytes and red blood corpuscles may require that the diameter of minute hole 43 be adjusted so that a suitable electrical signal is produced as a particle passes therethrough. One skilled in the art would have no difficulty in determining a suitable hole size, given the present disclosure.

One-directional clutches 24, 26, 28 and 30 allow the samplepreparation and measurement operations to be performed using a single reversible motor 16. Other techniques could be employed to achieve the same effect. For example, it is within the contemplation of the invention that both types of operation could be performed at the same time during a single rotation of shaft 10. However, the reversible operation of the preferred embodiment permits control system 11 to be built compactly and at low cost.

All of valves V1–V6 operate in essentially the same way. Thus, the following description of valve V1 will suffice as a complete description of all of the valves.

Figure 4:
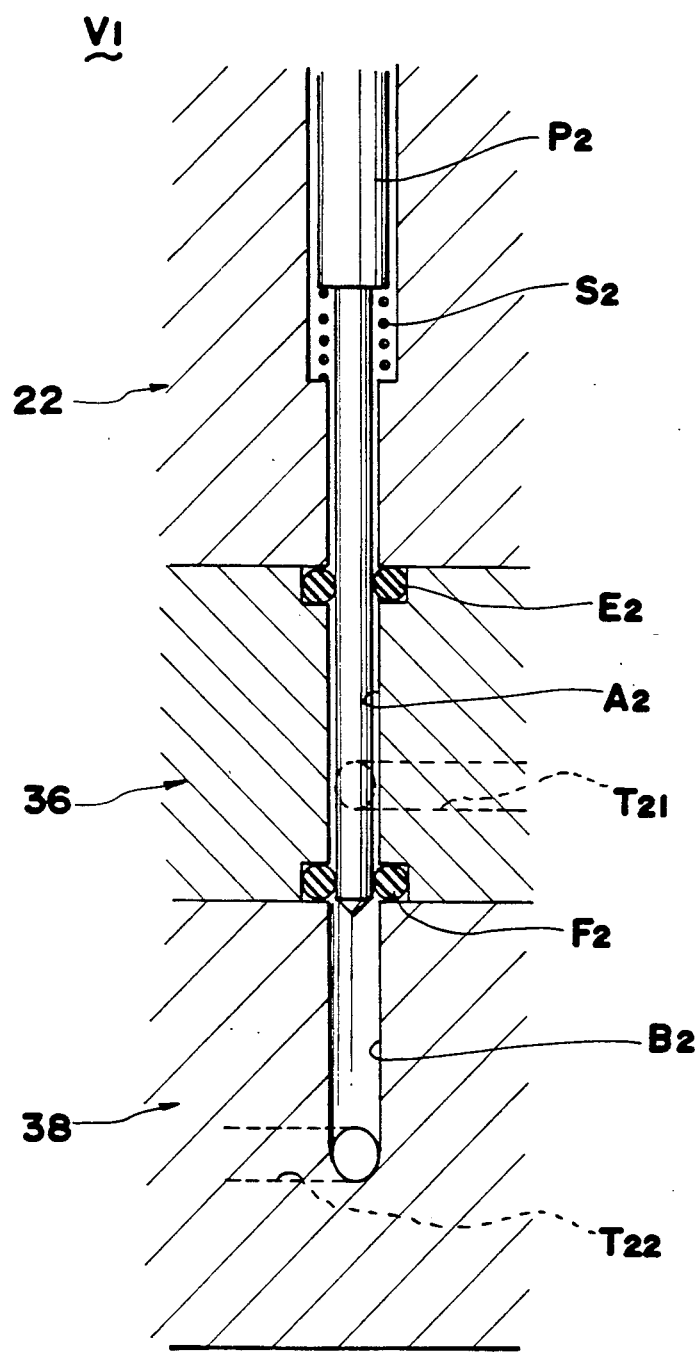
FIG. 4 is an enlarged cross section of one of the valves depicted in FIG. 2.

Referring now to FIG. 4, an O-ring E2 at the junction of supporter 22 and cylinder block 36 seals the junction between these two elements and also seals against piston P2. A second O-ring F2 at the junction of cylinder blocks 36 and 38 seals the junction between these two elements and against piston P2 to form a sealable chamber A2 between itself and O-ring E2. A path T21 enters the sealable chamber A2 through cylinder block 36. Chamber B2, below O-ring F2 is joined by a path T22.

When piston P2 is in the lowered (closed) position shown, O-ring F2 is in sealing contact with piston P2, and thereby prevents liquid communication between paths T21 and T22. When piston P2 is raised so that its peripheral surface is out of contact with O-ring F2, liquid communication between paths T21 and T22 is enabled. One end of tube 46 (FIG. 1) is connected to path T21. The other end of tube 46 passes into cylindrical detector 40. Path T21 is also connected to syringe C1. Path T22 is connected to isolating chamber Z1 (FIG. 1).

The embodiment of the present invention also allows elimination of errors caused by the presence of the air in the syringes. In particular, the expansion and contraction of air in syringe C4 can cause quantitative errors. The embodiment of the present invention shown in FIG. 5 eliminates the trapping of air bubbles which can lead to such errors.

Figure 5:
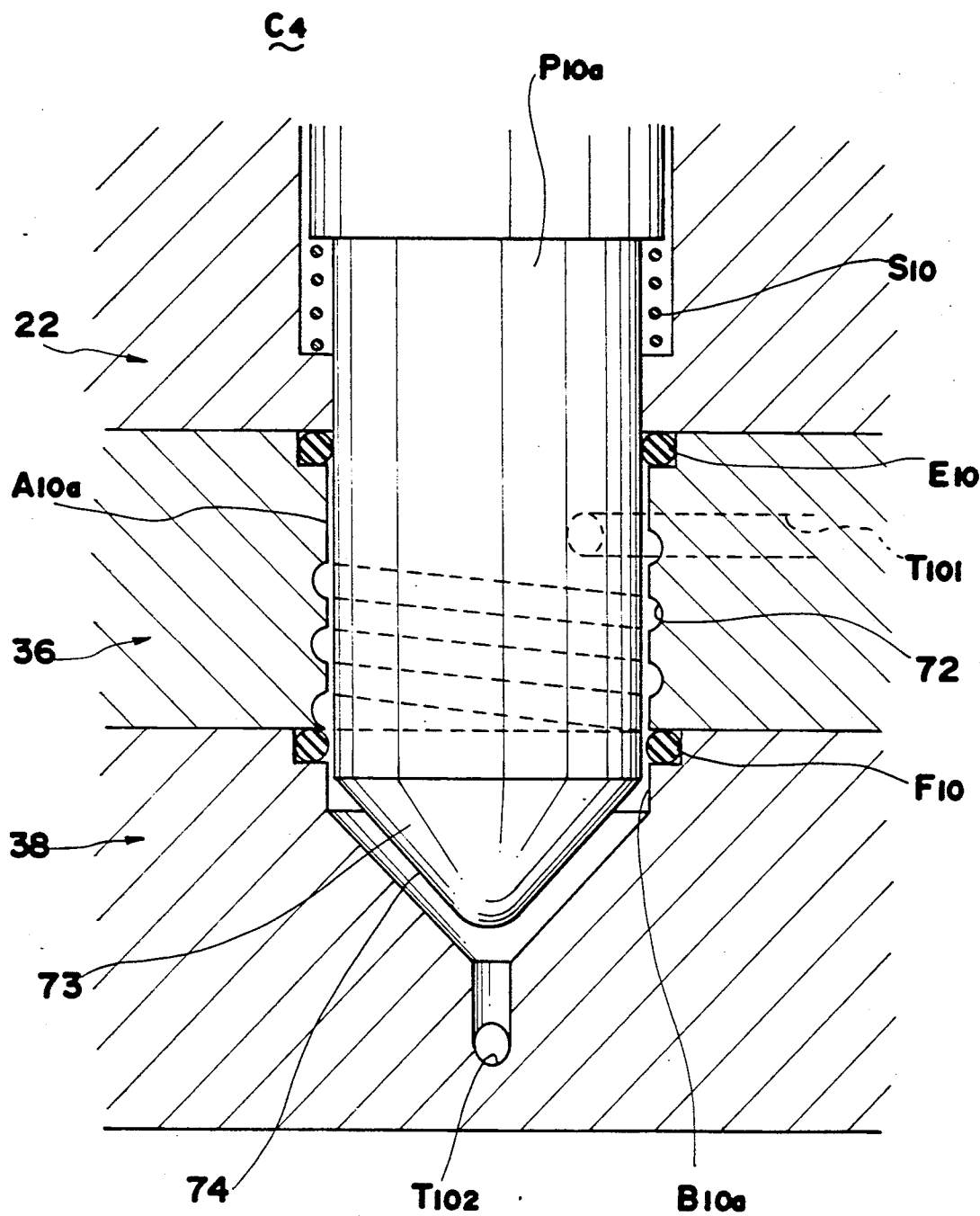
FIG. 5 is an enlarged cross section of one of the syringes depicted in FIG. 1.

Referring to FIG. 5, there is shown a piston P10a which, together with cavity B10a, forms syringe C4. The bottom 73 of piston P10a is a generally conical surface 74. Conical surface 74 of bottom 73 helps prevent the trapping of air bubbles below piston P10a by permitting them to float upward along its surface. A spiral groove 72 in the interior surface of cavity A10a helps the evacuation of trapped air bubbles. Therefore, bubbles of air travel up along conical surface 74 and then along spiral groove 72 to be ejected from syringe C4 through path T101.

One skilled in the art, with the present disclosure for reference, would be fully enabled to define the shapes of cams K1–K11 to perform the valve and fluid-displacement functions described herein. Thus, further description of the shapes of cams K1–K11 is omitted herefrom.

The apparatus for measuring the test liquid of the present invention has a number of advantages in comparison with prior art devices. It can be easily miniaturized, and its cost may be less.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A control system for controlling an analyzer of a liquid speciment comprising:

a plurality of cams;

means for rotating said plurality of cams;

a plurality of pistons mounted for moving in a plurality of cavities;

means for resiliently urging said plurality of pistons into contact with respective ones of said plurality of cams;

at least a first of said plurality of pistons including means for displacing a fixed quantity of said liquid specimen;

at least some of a remainder of said pistons including means for forming valves controlling a flow of said liquid displaced by said first of said plurality of pistons;

said means for rotating including at least one one-way clutch; and said at least one one-way clutch being effective for rotating at least some, but less than all, of said plurality of cams when said means for rotating rotates in one direction.

2. A control system of claim 1, wherein said at least one one-way clutch includes first and second one-way clutches;

said first one-way clutch being effective for rotating said at least some of said plurality of cams when said means for rotating rotates in a first direction;

said second one-way clutch being effective for rotating a remainder of said plurality of cams when said means for rotating rotates in a second direction; and said at least a first of said plurality of pistons includes a plurality of syringes.

3. A control system according to claim 2, wherein:

said plurality of cavities are disposed in at least one cylinder block; and said plurality of syringes and said plurality of valves are interconnected by pathways integrally formed in said cylinder block.

4. A control system according to claim 3 wherein said at least one cylinder block is at least first and second cylinder blocks with at least some of said cavities including aligned portions in said first and second cylinder blocks.

5. A control system for controlling an analyzer of a liquid specimen comprising:

a shaft;

a first plurality of cams;

a second plurality of cams;

a first one-way clutch on said shaft;

said first one-way clutch being of a type capable of transmitting torque from said shaft only during rotation of said shaft in a first direction;

means for connecting torque from said first one-way clutch to said first plurality of cams;

a second one-way clutch on said shaft;

said second one-way clutch being of a type capable of transmitting torque from said shaft only during rotation of said shaft in a second direction, opposite to said first direction;

means for connecting torque from said second one-way clutch to said second plurality of cams;

a first plurality of pistons mounted for moving in a first plurality of cavities, said first plurality of pistons contacting said first plurality of cams;

a second plurality of pistons mounted for movement in a second plurality of cavities, said second plurality of pistons contacting said second plurality of cams;

means cooperating with at least some of said pistons for forming syringes effective for displacing a quantity of said liquid; and means cooperating with at least some of a remainder of said pistons mounted for forming valves controlling a flow of said liquid displaced by said syringes.

6. A control system for controlling an analyzer of a liquid specimen comprising:

a shaft;

a first plurality of cams;

a second plurality of cams;

a first one-way clutch on said shaft;

said first one-way clutch being of a type capable of transmitting torque from said shaft only during rotation of said shaft in a first direction;

means for connecting torque from said first one-way clutch to said first plurality of cams;

a second one-way clutch on said shaft;

said second one-way clutch being of a type capable of transmitting torque from said shaft only during rotation of said shaft in a second direction, opposite to said first direction;

means for connecting torque from said second one-way clutch to said second plurality of cams;

a first plurality of pistons mounted for moving in a first plurality of cavities, said first plurality of pistons contacting said first plurality of cams;

a second plurality of pistons mounted for movement in a second plurality of cavities, said second plurality of pistons contacting said second plurality of cams;

means cooperating with at least some of said pistons for forming syringes effective for displacing a quantity of said liquid;

means cooperating with at least some of a remainder of said pistons mounted for forming valves controlling a flow of said liquid displaced by said syringes; and said syringes and valves are disposed in at least one cylinder block, and said syringes and valves are interconnected by paths in said cylinder block.

7. A control system of claim 6, wherein said at least one cylinder block includes two cylinder blocks assembled together.

8. A control system for controlling an analyzer of a liquid specimen comprising:

a shaft;

a first plurality of cams;

a second plurality of cams;

a first one-way clutch on said shaft;

said first one-way clutch being of a type capable of transmitting torque from said shaft only during rotation of said shaft in a first direction;

means for connecting torque from said first one-way clutch to said first plurality of cams;

a second one-way clutch on said shaft;

said second one-way clutch being of a type capable of transmitting
torque from said shaft only during rotation of said shaft in a second direction, opposite to said first direction;

means for connecting torque from said second one-way clutch to said second plurality of cams;

a first plurality of pistons mounted for moving in a first plurality of cavities, said first plurality of pistons contacting said first plurality of cams;

a second plurality of pistons mounted for movement in a second plurality of cavities, said second plurality of pistons contacting said second plurality of cams;

means cooperating with at least some of said pistons for forming syringes effective for displacing a quantity of said liquid;

means cooperating with at least some of a remainder of said pistons mounted for forming valves controlling a flow of said liquid displaced by said syringes;

at least one of said syringes includes a piston;

said piston being mounted for movement in a cavity;

said piston including a generally conical lower end;

said piston being disposed in a cavity; and a wall of said cavity including a groove in an inner surface thereof shaped to ease a passage of air from said cavity toward an outlet.

9. A control system of claim 8, wherein said groove is generally a spiral.

10. A control system for controlling liquid flow in a particle detector, comprising:

a plurality of cams, means for selectively rotating said plurality of cams in a selected one of a right-hand and a left-hand direction;

a plurality of pistons mounted for movement in a plurality of cavities;

said plurality of pistons contacting said plurality of cams; at least one of said plurality of pistons and one of said plurality of cavities forming a syringe effective for displacing a fixed quantity of the liquid; and at least some of a remainder of said plurality pistons and said plurality of cavities forming valves controlling a flow of the liquid displaced by said syringe.

11. A control system for controlling liquid flow in a particle detector, comprising:

a plurality of cams, means for selectively rotating said plurality of cams in a right-hand and a left-hand direction;

a plurality of pistons mounted for movement in a plurality of cavities;

said plurality of pistons contacting said plurality of cams; at least one of said plurality of pistons and one of said plurality of cavities forming a syringe effective for displacing a fixed quantity of the liquid;

at least some of a remainder of said plurality pistons and said plurality of cavities forming valves controlling a flow of the liquid displaced by said syringe;

said means for selectively rotating includes first means for selectively rotating a first portion of said plurality of cams only in a right-hand direction;

said means for selectively rotating includes second means for selectively rotating a remaining portion of said plurality of cams only in a left-hand direction; and said plurality of pistons including a first portion actuated by said first portion of said plurality of cams and a remainder actuated by said remaining portion of said plurality of cams, whereby syringe and valve actuation are separately performed.

* * * * *